(12) United States Patent
Jordan et al.

(10) Patent No.: US 9,365,857 B2
(45) Date of Patent: Jun. 14, 2016

(54) **XYLOSE ISOMERASE AND XYLITOL DEHYDROGENASE COMBINATION FOR XYLOSE FERMENTATION TO ETHANOL AND *B. FRAGILIS* XYLOSE ISOMERASE**

(75) Inventors: Sean Jordan, Decatur, IL (US); Beth Fatland-Bloom, Forsyth, IL (US); Lhing-Yew Li, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 157 days.

(21) Appl. No.: 13/996,305

(22) PCT Filed: Dec. 9, 2011

(86) PCT No.: PCT/US2011/064074
§ 371 (c)(1),
(2), (4) Date: Sep. 27, 2013

(87) PCT Pub. No.: WO2012/087601
PCT Pub. Date: Jun. 28, 2012

(65) Prior Publication Data
US 2014/0017768 A1    Jan. 16, 2014

Related U.S. Application Data

(60) Provisional application No. 61/426,575, filed on Dec. 23, 2010.

(51) Int. Cl.
| | |
|---|---|
| *C12P 7/06* | (2006.01) |
| *C12P 7/10* | (2006.01) |
| *C12N 9/90* | (2006.01) |
| *C12N 9/04* | (2006.01) |
| *C12N 1/19* | (2006.01) |
| *C12N 15/81* | (2006.01) |
| *C12N 9/92* | (2006.01) |

(52) U.S. Cl.
CPC .............. *C12N 15/81* (2013.01); *C12N 9/0006* (2013.01); *C12N 9/92* (2013.01); *C12P 7/10* (2013.01); *C12Y 101/01009* (2013.01); *C12Y 503/01005* (2013.01); *Y02E 50/16* (2013.01); *Y02P 20/52* (2015.11)

(58) Field of Classification Search
None
See application file for complete search history.

(56) References Cited

FOREIGN PATENT DOCUMENTS

WO    WO 2010074577 A1 *  7/2010

OTHER PUBLICATIONS

Traff et al., Deletion of the GRE3 aldose reductase gene and its influence on xylose metabolism in recombinant strains of *Saccharomyces cerevisiae* expressing the xylA and XKS1 genes, Appl. Environ. Microbiol., 2001, 67, 5668-74.*
Eliasson et al., Anaerobic Xylose Fermentation by Recombinant *Saccharomyces cerevisiae* Carrying XYL1, XYL2, and XKS1 in Mineral Medium Chemostat Cultures, Appl. Environ. Microbiol., 2000, 66, 3381-86.*
Kuyper et al., Evolutionary engineering of mixed-sugar utilization by a xylose-fermenting *Saccharomyces cerevisiae* strain, FEMS Yeast Res., 2005, 5, 925-34.*
GenBank, Accession No. NZ_JPHP01000032, 2014, www.ncbi.nlm.nih.gov.*
Singh et al., Primer premier: program for design of degenerate primers from a protein sequence, BioTechniques, 1998, 24, 318-19.*

* cited by examiner

*Primary Examiner* — Robert Mondesi
*Assistant Examiner* — Todd M Epstein
(74) *Attorney, Agent, or Firm* — Corey Crafton (57) ABSTRACT

Disclosed herein is a newly discovered problem and solution for engineering *S. cerevisiae* to ferment xylose to make ethanol utilizing xylose isomerase to convert xylose to xylulose for entry, via xylulokinase, into the pentose phosphate pathway. The problem is that when grown on a media containing xylose xylitol tends to accumulate in the cell despite the absence of xylose reductase activity in *S. cerevisiae*. Xylitol inhibits the activity of xylose isomerases. One solution described is to simultaneously express an exogenous xylitol dehydrogenase along with the exogenous xylose isomerase while optionally also overexpressing xylulokinase in the absence of expression of a xylose reductase. Another solution is a xylose isomerase from *Bacteroides fragilis* which is less inhibited by xylitol than other xylose isomerases, exemplified by *E. coli* xylose isomerase. Expression of the *Bacteroides fragilis* xylose isomerase may be used alone, or in combination with expression of a xylitol dehydrogenase and optionally over expression of xylulokinase to improve ethanol production from xylose.

9 Claims, 8 Drawing Sheets

Figure 7
Wild-type protein sequence of XylA from *Bacteroides fragilis*: SEQ. ID NO: 2

MATKEYFPGIGKIKFEGKDSKNPMAFRYYDAEKMINGRSMKDWLKFAMAWWHTLCAEGGDQFGGGTKQFPW
NGDPDPVQAAKNKMDAGFEFMQKMGIGYYCFHDVDLVTEADSIEAYEANLKELVAYAKQKQAETGIKLLWG
TANVFSHARYMNGAATNPDFDVVARAAVQIKNAIDATIELGGTNYVFWGGREGYMSLLNTDQKREKEHLAQ
MLTIARDYGRARGFKGTFLIEPKPMEPTKHQYDVDTETVIGFLKAHGLNQDFKVNIEVNHATLAGHTFEHE
LAVAVDNGMLGSIDANRGDYQNGWDTDQFPIDNFELTQAMMQIIRNDGLGNGGTNFDAKTRRNSTDPEDIF
IAHIAGMDAMARALESAANLLNESPYQKMLSDRYASFDAGKGKEFEEGKLSLEELVAYAKANGEPKQTSGQ
QELYEALVNIYSL

Figure 8
Mutant protein sequence of XylA from Bacteroides fragilis: SEQ. ID NO: 4.

MSTKEYFPGIGKIKFEGKDSKNPMAFRYYDAEKMINGRSMKDWLKFAMAWWHTLCAEGGDQFGGGTKQFPW
NGDPDPVQAAKNKMDAGFEFMQKMGIGYYCFHDVDLVTEADSIEAYEANLKELVAYAKQKQAETGIKLLWG
TANVFSHARYMNGAATNPDFDVVARAAVQIKNAIDATIELGGTNYVFWGGREGYMSLLNTDQKREKEHLAQ
MLTIARDYGRARGFKGTFLIEPKPMEPTKHQYDVDTETVIGFLKAHGLNQDFKVNIEVNHATLAGHTFEHE
LAVAVDNGMLGSIDANRGDYQNGWDTDQFPIDNFELTQAMMQIIRNDGLGNGGTNFDAKTRRNSTDPEDIF
IAHIAGMDAMARALESAANLLNESPYQKMLSDRYASFDAGKGKEFEEGKLSLEELVAYAKANGEPKQTSGQ
QELYEALVNIYSL

Figure 9
Wild type nucleotide sequence of XylA from Bacteroides fragilis: SEQ. ID NO: 1

ATGGCAACAAAAGAGTACTTCCCGGGTATAGGGAAAATTAAATTTGAAGGAAAAGACAGTAAGAACCCGAT
GGCATTTCGCTATTACGATGCCGAGAAAATGATTAACGGGCGTAGTATGAAAGATTGGTTAAAGTTTGCAA
TGGCATGGTGGCATACACTTTGTGCCGAAGGCGGTGACCAGTTTGGAGGCGGAACCAAACAGTTCCCATGG
AACGGTGACCCTGATCCCGTGCAGGCAGCCAAGAATAAAATGGATGCCGGTTTCGAGTTTATGCAGAAAAT
GGGCATCGGGTATTATTGCTTCCATGATGTCGATCTGGTTACGGAAGCCGACAGCATCGAAGCCTATGAGG
CCAACTTGAAAGAGCTGGTTGCTTATGCTAAGCAGAAACAGGCCGAAACAGGCATCAAACTGTTGTGGGGA
ACGGCCAATGTATTCAGCCACGCGCGTTACATGAACGGTGCAGCCACCAATCCCGATTTTGATGTTGTGGC
CCGTGCCGCTGTCCAGATAAAGAATGCGATTGATGCCACCATTGAACTGGGAGGTACGAACTATGTCTTTT
GGGGTGGACGCGAAGGCTATATGTCGTTGCTGAATACTGATCAGAAACGCGAAAAAGAACATCTGGCACAG
ATGCTGACCATTGCCCGTGATTATGGACGTGCACGTGGTTTCAAGGGCACTTTCCTGATTGAACCGAAACC
CATGGAACCGACAAAGCATCAGTATGATGTCGATACAGAGACAGTTATCGGCTTCCTGAAGGCTCACGGAC
TGAATCAAGACTTCAAAGTGAATATCGAAGTGAATCATGCCACCCTTGCAGGACATACGTTCGAACATGAA
CTGGCGGTGGCTGTAGACAACGGAATGTTGGGGTCTATCGACGCAAACCGCGGCGATTATCAGAACGGATG
GGATACGGATCAATTTCCGATTGACAACTTCGAACTGACACAAGCCATGATGCAGATTATCCGTAACGACG
GATTAGGTAACGGCGGTACAAACTTCGATGCCAAAACTCGCCGGAACTCTACTGACCCGGAAGATATCTTT
ATCGCACATATTGCCGGAATGGATGCTATGGCACGTGCCTTGGAAAGCGCAGCCAATCTGCTCAATGAGTC
TCCTTACCAGAAAATGTTGTCCGACCGTTATGCCTCGTTCGATGCGGGCAAAGGCAAGGAGTTCGAAGAAG
GGAAACTCAGCCTGGAGGAACTGGTTGCTTATGCCAAAGCCAACGGAGAGCCGAAGCAGACCAGCGGCCAA
CAGGAACTGTATGAAGCACTCGTTAATATCTACTCATTATAA

Figure 10
Nucleotide sequence encoding mutant XI from Bacteroides fragilis cloned via PCR. SEQ. ID NO: 3.

```
ATGTCTACAAAAGAGTACTTCCCGGGTATAGGGAAAATTAAATTTGAAGGAAAAGACAGTAAGAACCCGAT
GGCATTTCGCTATTACGATGCCGAGAAAATGATTAACGGGCGTAGTATGAAAGATTGGTTAAAGTTTGCAA
TGGCATGGTGGCATACACTTTGTGCCGAAGGCGGTGACCAGTTTGGAGGCGGAACCAAACAGTTCCCATGG
AACGGTGACCCTGATCCCGTGCAGGCAGCCAAGAATAAAATGGATGCCGGTTTCGAGTTTATGCAGAAAAT
GGGCATCGGGTATTATTGCTTCCATGATGTCGATCTGGTTACGGAAGCCGACAGCATCGAAGCCTATGAGG
CCAACTTGAAAGAGCTGGTTGCTTATGCTAAGCAGAAACAGGCCGAAACAGGCATCAAACTGTTGTGGGGA
ACGGCCAATGTATTCAGCCACGCGCGTTACATGAACGGTGCAGCCACCAATCCCGATTTTGATGTTGTGGC
CCGTGCCGCTGTCCAGATAAAGAATGCGATTGATGCCACCATTGAACTGGGAGGTACGAACTATGTCTTTT
GGGGTGGACGCGAAGGCTATATGTCGTTGCTGAATACTGATCAGAAACGCGAAAAGAACATCTGGCACAG
ATGCTGACCATTGCCCGTGATTATGGACGTGCACGTGGTTTCAAGGGCACTTTCCTGATTGAACCGAAACC
CATGGAACCGACAAAGCATCAGTATGATGTCGATACAGAGACAGTTATCGGCTTCCTGAAGGCTCACGGAC
TGAATCAAGACTTCAAAGTGAATATCGAAGTGAATCATGCCACCCTTGCAGGACATACGTTCGAACATGAA
CTGGCGGTGGCTGTAGACAACGGAATGTTGGGGTCTATCGACGCAAACCGCGGCGATTATCAGAACGGATG
GGATACGGATCAATTTCCGATTGACAACTTCGAACTGACACAAGCCATGATGCAGATTATCCGTAACGACG
GATTAGGTAACGGCGGTACAAACTTCGATGCCAAAACTCGCCGGAACTCTACTGACCCGGAAGATATCTTT
ATCGCACATATTGCCGGAATGGATGCTATGGCACGTGCCTTGGAAAGCGCAGCCAATCTGCTCAATGAGTC
TCCTTACCAGAAAATGTTGTCCGACCGTTATGCCTCGTTCGATGCGGGCAAAGGCAAGGAGTTCGAAGAAG
GGAAACTCAGCCTGGAGGAACTGGTTGCTTATGCCAAAGCCAACGGAGAGCCGAAGCAGACCAGCGGCCAA
CAGGAACTGTATGAAGCACTCGTTAATATCTACTCATTATAA
```

Figure 11
Synthetic nucleotide sequence encoding mutant XI from Bacteroides fragilis: SEQ. ID NO: 5.

```
TGTCTACGAAGGAATACTTCCCAGGCATCGGTAAGATCAAATTCGAAGGAAAGGATTCAAAGAATCCAATG
GCATTCAGATACTACGACGCTGAGAAGATGATCAACGGCAGAAGTATGAAGGACTGGTTGAAATTCGCAAT
GGCTTGGTGGCATACTCTTTGTGCCGAGGGTGGAGATCAATTTGGTGGAGGTACAAAGCAATTTCCATGGA
ACGGAGACCCAGATCCTGTCCAAGCTGCCAAGAATAAGATGGATGCTGGTTTTGAATTCATGCAAAAAATG
GGCATTGGGTATTACTGTTTCCATGATGTTGATTTGGTTACAGAAGCTGATTCTATCGAAGCTTACGAAGC
TAACTTGAAAGAATTAGTCGCCTATGCCAAGCAAAAGCAGGCTGAAACTGGCATTAAATTGTTATGGGGAA
CGGCAAATGTTTTCTCACACGCTCGTTATATGAATGGCGCTGCTACTAATCCGGATTTTGACGTTGTAGCA
AGAGCGGCTGTCCAAATCAAGAACGCTATTGATGCAACAATAGAATTAGGTGGGACTAATTATGTTTTTTG
GGGCGGCAGGGAAGGTTACATGAGCCTTCTGAACACCGACCAGAAAAGGGAAAAAGAGCACTTAGCCCAAA
TGTTGACTATCGCCAGAGATTACGGGAGAGCCAGAGGATTTAAAGGTACTTTCTTGATAGAACCTAAGCCT
ATGGAACCAACTAAACACCAATACGATGTCGATACTGAAACTGTTATTGGTTTTTTAAAAGCGCACGGTCT
AAATCAGGACTTTAAAGTTAACATAGAAGTTAATCACGCGACTCTAGCTGGTCACACTTTCGAGCATGAAC
TAGCAGTAGCTGTTGATAACGGAATGCTTGGCTCTATCGATGCAAACAGAGGTGATTATCAAAACGGTTGG
GATACCGATCAATTTCCAATCGATAATTTCGAGTTGACCCAAGCTATGATGCAAATCATTAGGAACGATGG
TTTAGGCAATGGAGGAACCAACTTTGATGCAAAGACTCGTAGAAACTCAACAGATCCCGAAGATATTTTCA
TTGCTCACATCGCTGGTATGGACGCAATGGCTAGAGCCTTAGAATCTGCTGCTAATCTGTTGAATGAAAGC
CCATACCAAAAGATGTTGAGCGACCGTTATGCCAGTTTTGACGCTGGAAAAGGAAAGGAATTCGAAGAAGG
TAAATTATCCTTGGAGGAGTTGGTTGCGTATGCAAAAGCTAATGGCGAACCAAAGCAAACGTCCGGTCAAC
AAGAATTGTATGAAGCTCTTGTGAATATTTACTCACTGTAA
```

XYLOSE ISOMERASE AND XYLITOL DEHYDROGENASE COMBINATION FOR XYLOSE FERMENTATION TO ETHANOL AND B. FRAGILIS XYLOSE ISOMERASE

CROSS REFERENCE TO RELATED APPLICATIONS

This application is a national phase entry of PCT application No. PCT/US2011/064074 filed Dec. 9, 2011, which claims priority to US Provisional Application No. 61/426,575 filed Dec. 23, 2010.

BACKGROUND OF THE INVENTION

The ability to produce ethanol from cellulosic feedstocks by fermentation on a commercial scale is a long sought goal. To be economical, the amount of ethanol produced must be sufficient to be worth the cost of preparation of the feedstock and processing of the final product. To produce sufficient amounts of ethanol requires a fermentation organism that is biologically efficient at ethanol production in comparison to production of other metabolic products. Efficiency is determined by yield and productivity, yield being expressed as a weight percentage of sugar feedstock (typically sucrose or glucose) converted into ethanol, and productivity being expressed as the maximum amount of ethanol that can be produced as a volume/volume percentage of the fermentation media before the fermentation ceases due to ethanol toxicity. In this regard, by far, the most efficient ethanol producing microorganism is the baker's yeast *S. cerevisiae*

Efficient ethanol producing strains of *S. cerevisiae* are capable of converting 90-93% of a sugar based carbon source into ethanol on wt/wt basis and the ethanol can typically accumulate to 16-17% of the volume of the fermentation media. The sugar for commercial scale production of ethanol is conventionally obtained by extraction of sucrose from sugar beet or cane, or by hydrolysis of corn starch to produce glucose. Sucrose and corn starch, however, represent only a small fraction of the total sugars in plant material, most of which is contained in the β glucoside polymers cellulose and hemicellulose, the later being a branched polymer of the C6 sugars glucose and mannose and the C5 sugars xylose and arabinose.

There are several methods in the art for making hydrolysates of cellulose and hemicelluloses to produce feedstocks containing glucose, mannose, xylose and arabinose. For typical hydrolysates from corn stover, glucose represents 14.4%, mannose 0.9%, xylose 66.1% and arabinose 11.8% of the sugars. For typical hydrolysates of corn fiber glucose represents 48.6% xylose 25.2% and arabinose 17.6% of the sugars. Glucose and mannose are efficiently converted to ethanol during natural anerobic metabolism, however, *S. cerevisiae*, lacks the enzymatic machinery to convert the dominant sugar, xylose, into ethanol. To do so requires genetic engineering of *S. cerevisiae* to express metabolic enzymes that can convert xylose into xylulose phosphate—a C5 metabolite that is part of the pentose phosphate pathway, which ultimately produces intermediates that can enter the glycolytic pathway and be converted to ethanol during anaerobic fermentation. Normally within the pentose phosphate pathway, xylulose phosphate is derived from ribulose phosphate by the action of an epimerase, but in addition, *S. cerevisiae* contains the enzyme xylulokinase which can directly phosphorylate xylulose. Xylulose however, is a rare metabolite, and the level of expression of xylulokinase in *S. cerevisiae* is low. But more importantly, xylulokinase does not phosphorylate xylose and *S. cerevisiae* lacks the necessary enzymes to convert xylose to xyululose so is unable to utilize xylose as a carbon source without metabolic engineering.

There are two approaches to engineer *S. cerevisiae* to produce xylulose from xylose. The first represented by U.S. Pat. No 5,789,210 to Ho et al, is the XR-XD-XK three gene route, which is to overexpress xylulokinase (XK) simultaneously with an exogenous xylose reductase (XR) which reduces xylose to xylitol, and a xylitol dehydrogenase (XD), which oxidizes xylitol to xylulose. This approach, however, creates a redox imbalance in *S. cerevisiae* because xylose reductase utilizes NAD(H) as the reducing cofactor while xylitol dehydrogenase uses NADP$^+$ as the oxidizing cofactor. This imbalance negatively affects the growth and productivity of *S. cerevisiae* shutting down efficient production of ethanol from xylose. One option to overcome this problem is to use a mutant xylose reductase that has a lower $K_m$ for NAD$^+$ than NADP$^+$ thereby restoring the redox balance as has been described for example by Petschacher B, et. al. (Biochem J2005, 385:75-83).

The second approach is the XI-XK two gene route, which is to overexpress xylulokinase along with an exogenous xylose isomerase (XI) which directly converts xylose to xylulose without reduction and subsequent oxidation. This approach is represented by: U.S. Pat. No. 7,622,284 and US Pat. Pub Nos: US20060216804, US20080261287. Genes from a variety of bacterial and fungal source of xylose isomerase share the common name xylA. Several species of xylA genes have been identified from bacterial and fungal sources and some, but not all, have been shown to be useful in producing ethanol from xylose simultaneously overexpressed with xylulokinase. Proposed bacterial sources for such xylA genes include *Thermus thermophilus* (U.S. Pat. No. 7,622,284), *Bacteroides thetaiotaomnicron*, (US20060216804, US20080261287) and *Xanthamonus*. Several fungal sources of xylA genes have also been proposed, including from *Neocallimastix, Caecomyces, Piromyces, Orpinomyces*, or *Rumnomyces*. (US20080261287). See also Curr Op Biotech 17:320 (2006). Of these, only the xylA genes from *Piromyces* (20080014620) *Orpinomyces* (Madhavan A, Tamalampudi S, Ushida K, Kanai D, Katahira S, Srivastava A, Fukuda H, Bisaria VS, Kondo A. Appl Microbiol Biotechnol. 2009 82(6):1067-78.) and *Bacteroides thetaiotaomnicron* (US20080261287) have been shown to improve ethanol production in *S. cerevisiae* when co-overexpressed with xylulokinase. See also FEMS Yeast Res 4:69, FEMS Yeast Res 5:399, FEMS Yeast Res 4:655, FEMS Yeast Res 5:925.

Although ethanol production from both the three gene approach and the two gene approach has been demonstrated, the ethanol yield form xylose remains lower than expected for strains only containing those features. To improve productivity requires further genetic manipulation, either by way of mutation, evolutionary selection or by further genetic engineering. For example, US20070082386 proposes that ethanol production from xylitol by either the two gene or three gene route could be improved by increasing expression of a xylose transporting enzyme and/or by overexpression of genes encoding enzymes of the pentose phosphate pathway. US20060234364 discloses that mutants having a deletion in an endogenous gre3 gene encoding a non specific aldol reductase could improve ethanol production from xylitol using the two gene approach. US20070155000, from a different perspective, teaches than ethanol production from xylose containing hydrolysates utilizing the two gene route could be improved by further selection for resistance against growth inhibitors such as furfural and hydroxymethyl furfural that are typically found in hydrolysates of lignocellulosic biomass.

There remains a need in the art to discover other xylose isomerase genes and other multi gene combinations to improve the efficiency of xylose utilization in *S. cerevisiae* for ethanol production. The disclosure that follows presents such alternatives in the form of a particular xylose isomerase xylA gene from *Bacteroides fragilis* and alternative three gene route that includes simultaneous overexpression of an xylose isomerase, xylitol dehydrogenase and xylulokinase activity, without the need for overexpressing xylose reductase.

SUMMARY OF THE INVENTION

Described herein are recombinant yeast strains and methods of producing ethanol therefrom where xylose is a carbon source for growth and ethanol production. One broad aspect includes *S. cerevisiae* strains having a recombinant nucleic acid comprising a sequence encoding an exogenous xylose isomerase and an exogenous xylitol dehydrogenase, each operably linked to a promoter to over express the exogenous genes; with the proviso the strain does not also overexpress and exogenous xylose reductase activity in the *S. cerevisiae* strain. One feature of an exemplary exogenous xylose isomerase is that it is less inhibited by xylitol than is a homologue xylose isomerase from *E. coli*. One particular example is a xylose isomerase derived from a xylA gene from a strain of *Bacteroides fragilis*. Exemplary sequences and vectors encoding such genes are also described. These aspects may optionally be included with yeast strains that also over-express a xylulokinase activity.

Another aspect is yeast strains obtained by evolutionary selection of the forgoing types of parent strains. The evolutionary selection includes expressing in a parent yeast strain, a nucleic acid encoding an exogenous xylose isomerase operably linked to a promoter to express the exogenous xylose isomerase in the parent yeast strain. Performing a first growing of the parent yeast strain in a liquid media containing xylose as a principle carbon source to produce a population of offspring yeast strains. performing a second growing of the population of the offspring yeast strains on a solid media containing xylose as a principle carbon source. The selection is to obtain a fast growing daughter strain from the offspring yeast strains, characterized in the fast growing daughter yeast strains grow faster than other yeast in the population of offspring yeast strains on the solid media. The steps of first and second growing and selection are repeated to finally obtain a final selected yeast strain that produces more ethanol from xylose than the parent yeast strain. The method is exemplified with a yeast strain herein the xylose isomerase is encoded by a xylA gene of *B. fragilis*. The method may further be implemented when the parent strain further expresses a nucleic acid encoding an exogenous xylitol dehydrogenase operably linked to a promoter to express the exogenous xylitol dehydrogenase in the parent yeast strain. An exemplary strain made by such a process is described in the Figures as Y500+ bsd+XIbf "e" and deposited as strain number NRRL Y-50424.

BRIEF DESCRIPTION OF THE DRAWINGS

FIG. 1 illustrates growth (OD600) of *S. cerevisiae* flask cultures growing on YEP media+2% xylose over time (hours). All strains were derived from parent ethanol producing strain Y500 and each carries a blasticidin resistance marker (bsd). 421 i is a transformant carrying the XI (xylA) from *Bacteroides fragilis* driven by the HXT7 promoter from *S. cerevisiae* and has been deposited under terms of the Budapest Treaty at the Agricultural Research Services Northern Regional Research Laboratories as deposit number NRRL Y-50423 on Oct. 12, 2010. 437i carries the same XI and XD (xyl2) from *Pichia stipitis* driven by the *P. stipitis* XD promoter also deposited with number NRRL Y-50424. 437: xks carries the same XI and XD plus carries an extra copy of the XKS (xks) from *S. cerevisiae* also deposited with number NRRL Y-50425.

FIG. 7 shows the wild type protein sequence for XI from the xylA gene *B. fragilis* (SEQ. ID NO: 2).

FIG. 8 shows the mutant protein sequence for XI from the xylA gene of *B. fragilis* where a change in the nucleotide sequence to enhance transcription results in a mutant protein where a serine substitutes for the alanine at position 2 (SEQ. ID NO: 4).

FIG. 9 shows the wild type nucleotide sequence for xylA from *B. fragilis*. (SEQ. ID NO: 1)

FIG. 10 shows the mutant nucleotide sequence (SEQ. ID NO: 3) encoding the mutant xylA according to SEQ. ID NO: 4.

FIG. 11 shows another the mutant nucleotide sequence (SEQ. ID NO: 5) also encoding the mutant xylA according to SEQ. ID NO: 4 optimized for expression in *S. cerevisiae*.

DETAILED DESCRIPTION OF THE INVENTION

The following description and forgoing Background make citations to certain references that may aid one of ordinary skill in the art understand the present invention and that may provide materials, information, techniques, proteins, vectors and nucleotide sequences that may assist one of ordinary skill in the art to make and use aspects of the present invention in its fullest scope. Accordingly, each cited reference is incorporated into this application as if originally filed herewith to the extent the teaching of the cited references do not conflict with the teaching of the present application, in which case the teaching of this application shall be deemed to control over the conflicting teaching of art incorporated herein by reference.

One aspect of the invention is discovery that the xylose isomerase from *Bacteroides fragilis* is less sensitive to xylitol inhibition than are other xylose isomerase. Examples of other xylose isomerases include, but are not limited, those from the fungi *Piromyces* or *Orpinomyces* or from the sibling bacterial isomerases from *E. coli, L. lactis* and *Bacteroides thetaiotaomnicron* that have been previously described in the art. Two *B. fragilis* xylose isomerases of the present invention with reduced sensitivity to xyitol inhibition have the peptide sequences according to SEQ. ID NOS:2 and 4 shown in FIGS. 7 and 8 respectively. SEQ. ID NO: 2 is a wild type sequence for the xylA gene from *B. fragilis* which was isolated by the present inventors and which is encoded by nucleotide sequence according to SEQ. ID NO: 1 shown in FIG. 9. SEQ. ID NO: 4 is a mutant xylA made by the present inventors to enhance transcription in *S. cerevisiae* and which is encoded by the nucleotide sequence according to SEQ. ID NO: 3 shown in FIG. 10. The XI proteins according to SEQ. ID NO: 2 and 4 are identical except that the mutation to enhance transcription also results in a change of an alanine to a serine at position 2 of the protein according to SEQ ID NO:4. SEQ. ID NO: 4 is also encoded by SEQ. ID NO: 5 shown in FIG. 11 which preserves the change in nucleotide sequence for enhancement of transcription, but which also has changes in codon usage to optimize for protein synthesis in *S. cerevisiae*. The *B. fragilis* XI proteins according to SEQ. ID NO: 2 and 4 are only 78.5% identical to the protein sequences for XI from *Piromyces*, 77.9% identical to the sequence from *Orpinomyces*, 46.2% identical to the sequence from *L. lactic*, 52.5% identical to the sequence from *C. difficile*, 47.3% identical to the sequence from *E. coli*, and 90% identical to the sequence from *Bacteroides thetaiotamnicron*. Accordingly, a *B. fragilis* XI useful for the present invention has greater than 90%, greater than 92.5%, greater than 95%, or greater than 98% amino acid sequence identity to SEQ.ID NO: 2 or SEQ.ID NO: 4.

Figure 3:
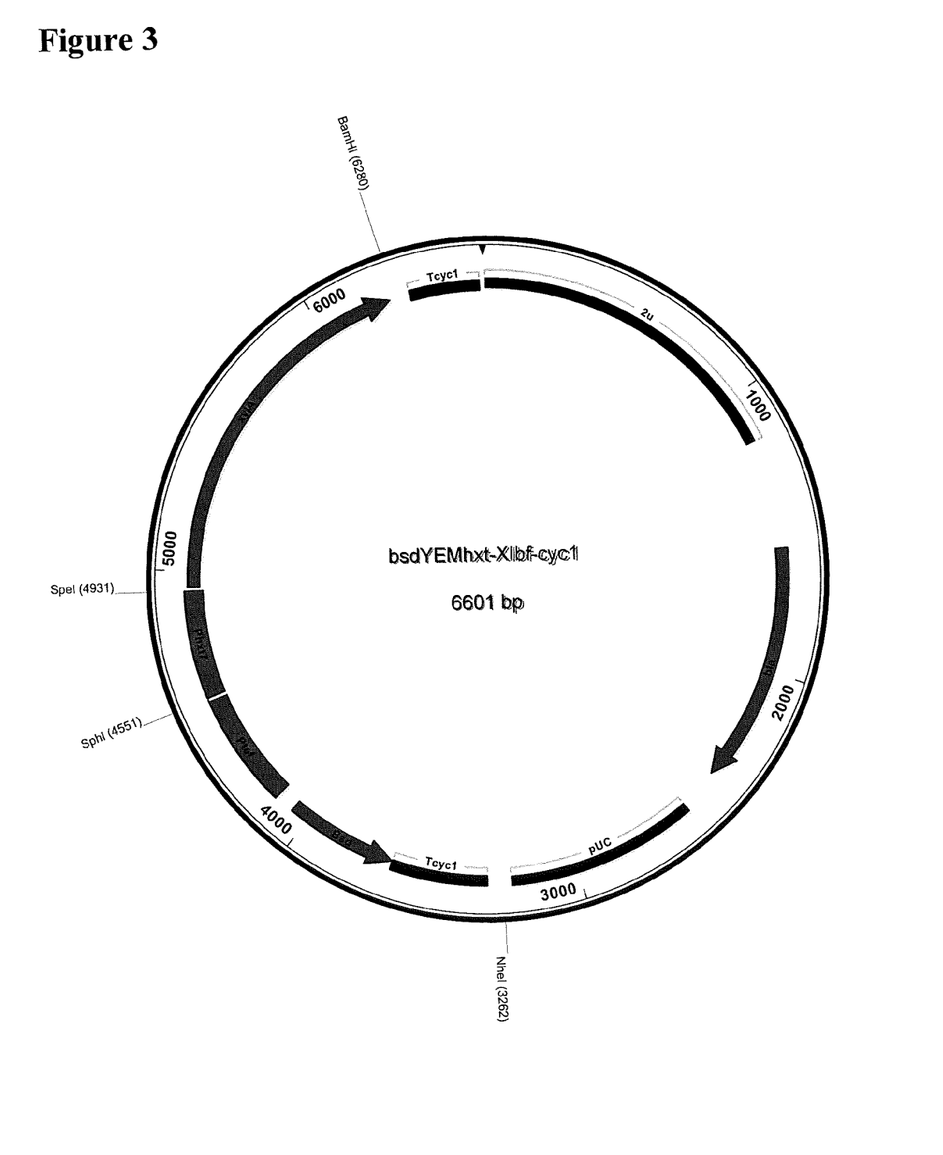
FIG. 3 depicts a plasmid map of bsdYEMhxt-XIbf-cycl, which is a yeast replicating plasmid carrying xylA from *B. fragilis* under control of the *S. cereiviase* hxt7 promoter.

A distinguishing feature of the *B. fragilis* isomerases described herein is that enzymes are less inhibited by xylitol than orthologue XI sequences from other organism. FIG. 3 shows a comparison of the xylitol inhibition of XI from *B. fragilis* according to SEQ. ID NO: 4 in comparison to its *E. coli* orthologue. At 12.5 mM xylitol, the *E. coli* XI activity is >97% inhibited, in contrast to the *B. fragilis* XI, which retains at least 30% of its activity at the same xylitol concentration.

While the precise differences in protein structure that accounts for the lower inhibition by xylitol for the *B. fragilis* enzyme is not presently known, the relationship between the structural and more important functional differences can be characterized in various ways. One characterization of the scope of the *B. fragilis* XI provided herein, is that it is a protein encoding a xylose isomerase activity to convert xylose to xylulose and having at least 90% identity to SEQ. ID NO: 2 or 4. Another is that it is a protein encoding a xylose isomerase activity to convert xylose to xylulose and that is more identical to SEQ. ID NO: 2 or 4 than to a XI protein sequence from *Piromyces, Orpinomyces, E. coli*, or *Bacteroides thetaiotaomnicron*. Yet another characterization is that is a protein encoding a xylose isomerase activity to convert xylose to xylulose that is less inhibited by xylitol than a XI protein sequence from *Piromyces, Orpinomyces, E. coli*, or *B. thetaiotaomnicron*. The polynucleotides provided herein track the same functional definitions as being nucleotide sequences that encode such functional proteins as characterized above, and/or that would hybridize to SEQ. ID NO: 1, 3 or 5 under stringent hybridization conditions under which they would not hybridize to a nucleotide sequences encoding a protein with XI activity from *Piromyces, Orpinomyces* or *Bacteroides thetaiotaomnicron*.

Figure 5:
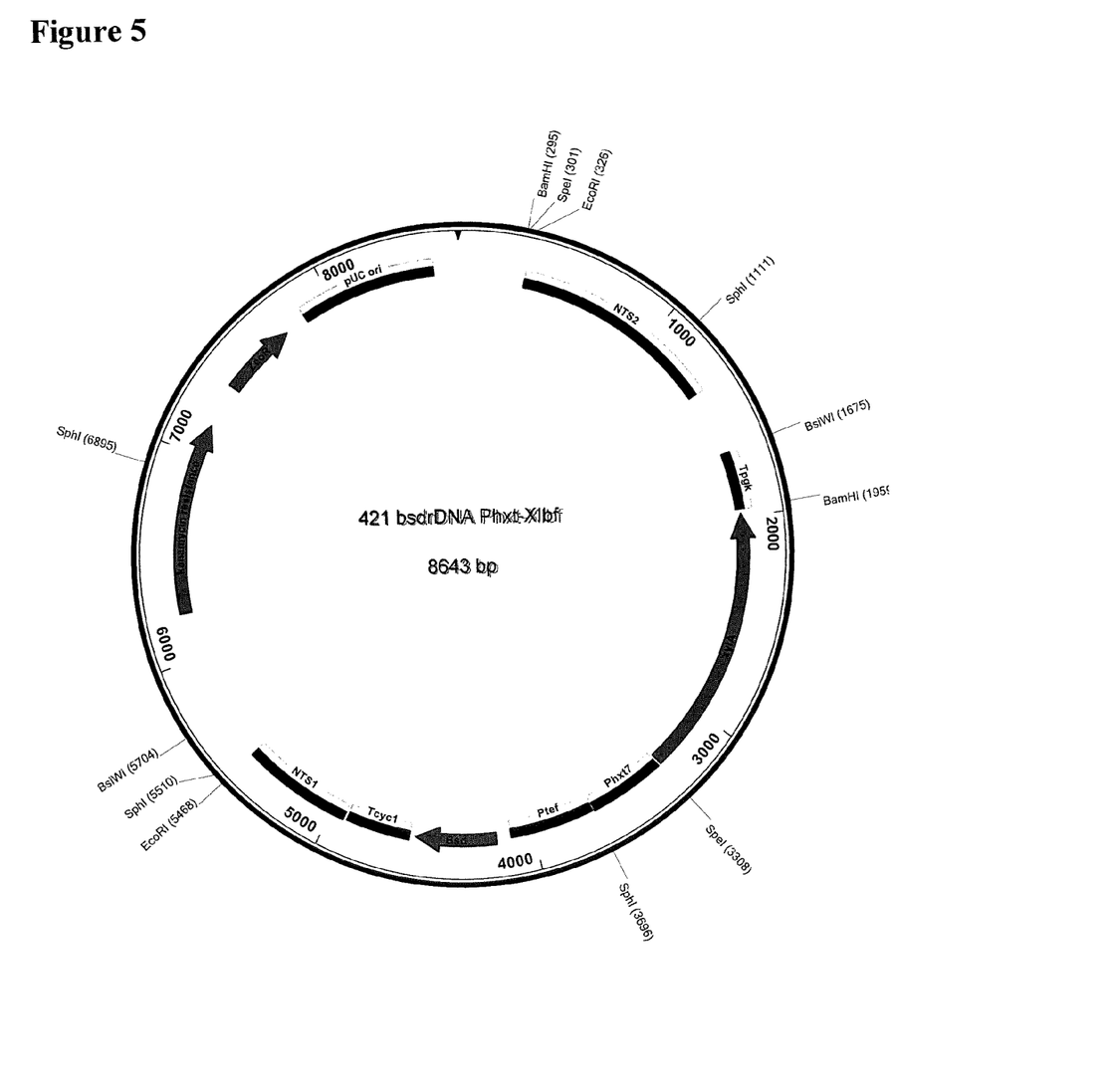
FIG. 5. depicts a plasmid map of plasmid 421, which is a yeast integrative vector used to cross xylA from *B. fragilis* under control of the yeast hxt7 promoter and blasticidin resistance into the chromosome of *S. cerevisiae*.
Figure 6:
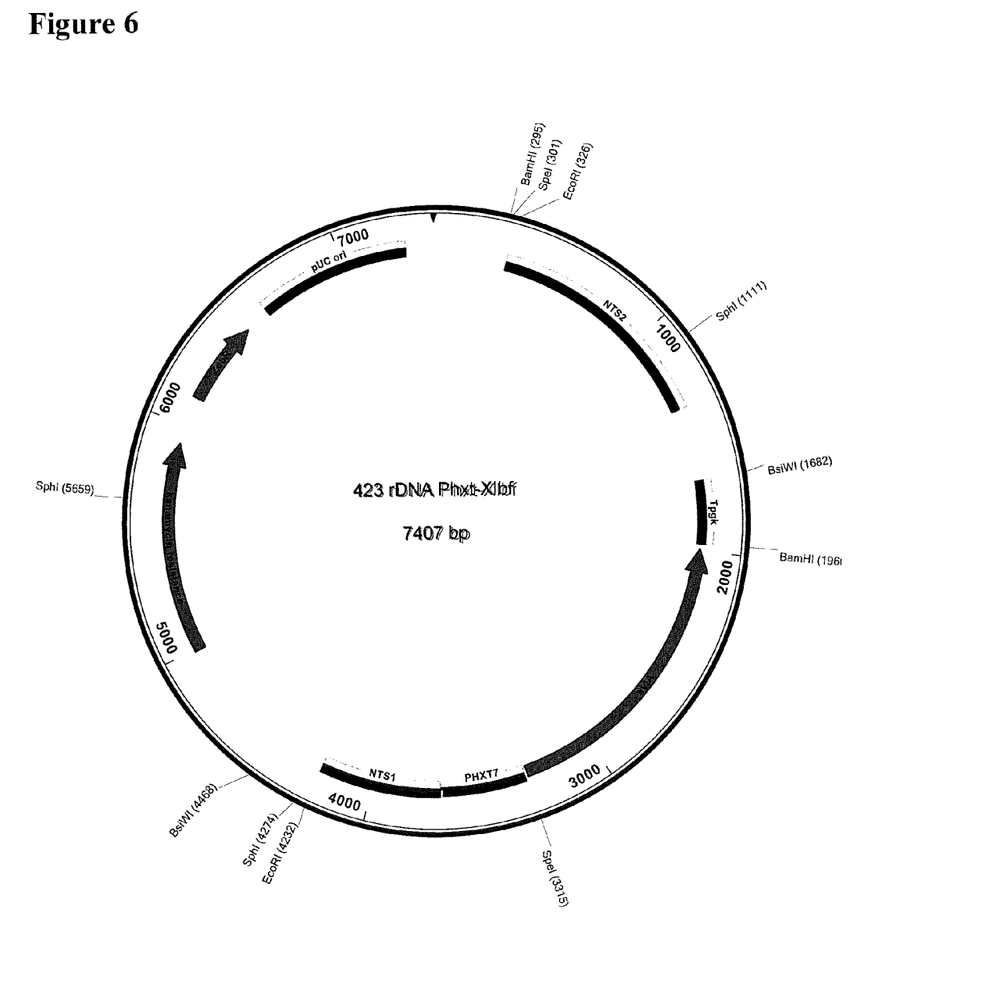
FIG. 6. depicts a plasmid map of plasmid 426, a yeast integrative vector used to cross xylA from *B. fragilis* under control of the yeast hxt7 promoter into the chromosome of *S. cerevisiae*.

Another aspect of the present teaching is use of the forgoing *B. fragilis* XI genes and proteins expressed thereby to engineer *S. cerevisiae* for the production of ethanol from xylose. In a first embodiment, a xylA polynucleotide according to SEQ. ID NO: 5 encoding the XI protein according to SEQ. ID NO:4 was operably linked to the *S. cerevisiae* hxt7 promoter and cyc terminator in the multicopy autonomously replicating yeast plasmid bsdYEMhxt-XIbf-cycl shown in FIG. 3. In other embodiments, the same transcriptional unit for expression of the *B. fragils* XI protein was also engineered into integrating plasmids 421 bsd rDNA Phxt-Xibf (the 421 construct) and 423 rDNA Phxt-XIbf (the 423 construct) shown in FIGS. 5 and 6, respectively. Each of these integrative plasmids contains nucleotide sequences for yeast ribosomal RNA genes for targeted recombination into the chromosome in a region encoding a ribosomal RNA, which are multicopy genes in *S. cerevisiae*. The 423 plasmid carries the marker gene for kanomycin resistance, while the 421 plasmid additionally carries the marker gene bsd, conferring resistance to the fungicide blasticidin.

Figure 1:
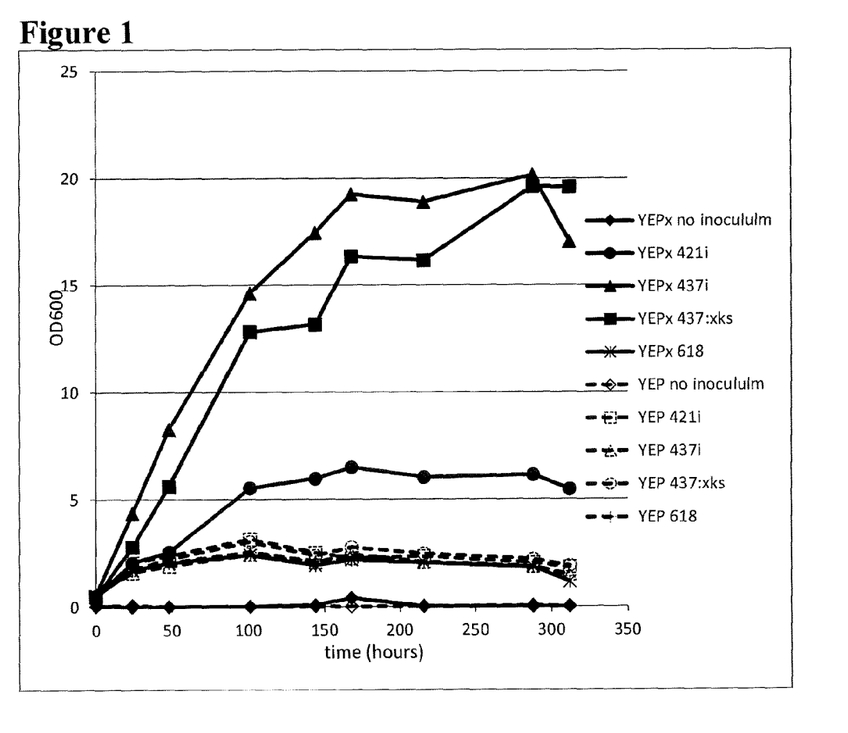
Figure 2:
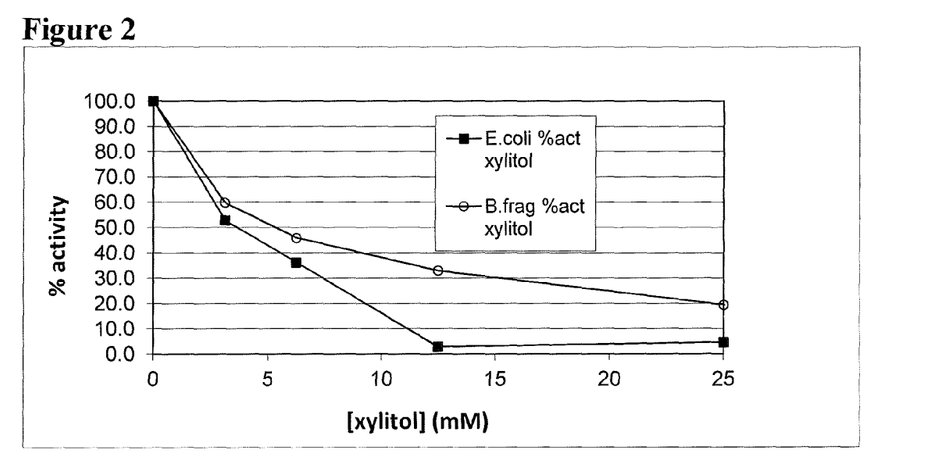
FIG. 2 shows a comparison of *E. coli* xylose isomerase and *B. fragilis* xylose isomerase activity in the presence of varying concentrations of xylitol. Activity is reported as the percent of activity obtained in the absence of xylitol.

The 421 construct was integrated into the chromosome of a parent *S. cerevisiae* strain Y500, which is an exemplary commercial ethanol producing yeast strain. This commercial strain has characteristics typical of other commercially available strains such as Ethanol Red™, available from Lesaffre Group (Cedar Rapids Iowa) in terms of ethanol productivity. Transformants containing the 421 construct were selected for blasticidin resistance. An initial transformant referred to in FIG. 1 as 421i was tested for its ability to grow in flasks on media containing yeast extract and peptone (YEP) with 2% wt/v xylose as the sole carbon source in comparison to a control containing the same bsd vector, but lacking the *B. fragilis* XI coding region (Y500+bsd). As shown in FIG. 1, the control strain ceased growth in YEP media within the first few hours, presumably after exhaustion of residual carbon sources from the YEP media. In contrast, the strain bearing the 421 construct expressing the *B. fragilis* XI continued growth on xylose for period of at least 150 hours.

Another aspect of the present invention is recognizing that one of the problems with the xylose isomerase/xylulokinase two gene route for the production ethanol from xylose is unexpected accumulation of xylitol within the cell. This is a surprising finding because *S. cerevisiae* does not naturally contain a xylose reductase activity. While not be bound by theory, it is believed that the activity of one or more non specific aldol reductases, such as those encoded by the gre3 gene of *S. cerevisiae* may be converting a significant portion of the aldol sugars, including xylose, into xylitol. Because as mentioned above, xylitol is an inhibitor of xylose isomerases, the intracellular accumulation of xylitol may inhibit the isomerization of xylose to xylulose, slowing the production of ethanol from xylitol. US Pat. Pub No 20080261287 may at least partially address this problem in another system by deletion of the gre3 gene while simultaneously overexpressing a *Piromyces* xylose isomerase xylA gene in *S. cerevisiae* However, despite reporting that such strains hardly accumulate xylitol, ethanol yields from xylose remains low, which the present inventors believe is due to other factors that may cause the accumulation of xylitol.

To compensate for this, one embodiment of the invention is to simultaneously express an exogenous xylitol dehydrogenase along with the exogenous xylose isomerase. This represents a novel 2 gene solution in that while xylose is indirectly being driven to xylulose by XI, simultaneously, the non specifically accumulated pool of xylitol is also being swept toward xylulose by XD preventing the inhibition of XI conversion of xylose to xylulose by xylitol.

Figure 4:
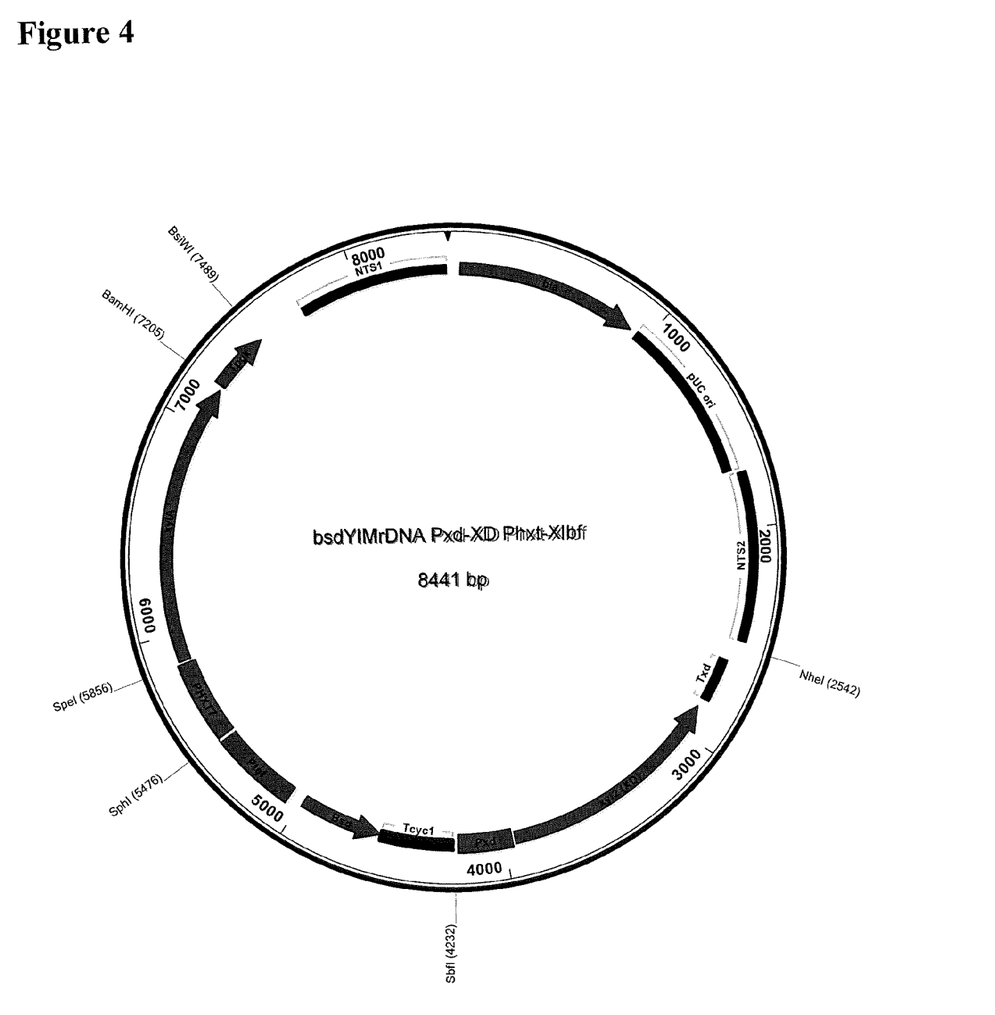
FIG. 4. depicts a plasmid map of bsdYIMrDNA Pxd-XD Phxt-XIbf, which is an integrative vector used to cross xylA from *B. fragilis* under control of the *S. cerevisae* hxt7 promoter and XD from *Pichia stipitis* (see U.S. Pat. No 5,789, 210) under the control of the *P. stipitis* xd promoter into the chromosome of *S. cerevisiae*.

Y500 was engineered with the chromosomal integration vector, plasmid bsdYIMrDNA.Pxd-XD Phxt-Xibf (437), shown in FIG. 4. This plasmid carries the bsd, resistancegene, the xylA gene encoding XI from *B. fragilis* operably linked under the control of the yeast Hxt7 promoter, as in the 421 and 423 constructs mentioned above, but further carries the xyl2 gene from *P. stipitis* (see U.S. Pat. No. 5,789,210) encoding XD operably linked under control of the *P. stipitis* XD promoter. Blasticidin resistant strains having his vector integrated into the Y500 chromosome were selected and tested for the ability to utilize xylose for growth and to ferment xylose to produce ethanol.

FIG. 1 shows the growth of the XI/XD construct 437 in shake flasks on media containing 2% xylose as the sole added carbon source in comparison to the control strains Y500, Y500 expressing XD alone, and Y500 expressing XIbf alone. The growth rate of the strain expressing both XI and XD was enhanced over each of the control strains.

The solution of simultaneously expressing XI and XD can advantageously also be implemented with a three gene solution that further includes over-expressing xylulokinase (XK). Unlike the three gene route using the combination of xylose reductase and xylitol dehydrogenase and over-expressed xylulokinase, the present invention does not require, and indeed, preferably omits expression of a xylose reductase activity. Over-expression of XK would improve ethanol production from xylose in cases where the over-accumulation of xyulose is rate limiting. Such a condition may be the case where one or more of the XI or XD activities are also over-expressed, or when those activities have been modified to produce a higher turnover number or reduced allosteric inhibition.

What is claimed is:

1. A *S. cerevisiae* strain having a recombinant nucleic acid comprising a sequence encoding the exogenous xylose isomerase according to SEQ ID NO:4 and an exogenous xylitol dehydrogenase encoded by a xyl2 gene from *P. stipitis*, each operably linked to a promoter to over express the exogenous xylose isomerase and exogenous xylitol dehydrogenase; with the proviso the strain does not also overexpress an exogenous xylose reductase activity in the *S. cerevisiae* strain.

2. The *S. cerevisiae* strain of claim 1 wherein the exogenous xylose isomerase is less inhibited by xylitol than is a homologue xylose isomerase from *E. coli*.

3. The *S. cerevisiae* strain of claim 1 wherein the exogenous of the exogenous xylose isomerase is derived from a xylA gene from a strain of *Bacteroides fragilis*.

4. The *S. cerevisiae* strain of claim 1 wherein the nucleic acid encoding the exogenous xylose isomerase comprises a sequence selected from the group consisting of SEQ ID NO. 3 and SEQ ID NO. 5.

5. The *S. cerevisiae* strain of claim 1 wherein said strain further includes a nucleic acid operably linked to a yeast promoter to over-expresses a xylulokinase activity in the strain.

6. The *S. cerevisiae* strain of claim 1 wherein said strain produces more ethanol by fermentation of xylose than an otherwise identical strain that overexpresses xylose isomerase and xylulokinase, but does not overexpress the exogenous xylitol dehydrogenase.

7. The *S. cerevisiae* strain of claim 1 wherein at least one of the recombinant nucleic acids encoding the exogenous xylose isomerase and the exogenous xylitol dehydrogenase is integrated into the genome of the *S. cerevisiae* strain.

8. The *S. cerevisiae* strain of claim 7 wherein at least two of the recombinant nucleic acids encoding the exogenous xylose isomerase and the exogenous xylitol dehydrogenase are integrated into the genome of the *S. cerevisiae* strain; and the strain includes a nucleic acid encoding a xylulokinase enzyme operably linked to a promoter to overexpress the xylulokinase also integrated into the genome.

9. The *S. cerevisiae* strain-of claim 1 which is the strain Y500+bsd+XIbf "e" described in the specification and deposited as NRRL Y 50424.

* * * * *

SEQUENCE LISTING

```
<160> NUMBER OF SEQ ID NOS: 5

<210> SEQ ID NO 1
<211> LENGTH: 1320
<212> TYPE: DNA
<213> ORGANISM: Bacteroides fragilis

<400> SEQUENCE: 1
atggcaacaa aagagtactt cccgggtata gggaaaatta aatttgaagg aaaagacagt      60
aagaacccga tggcatttcg ctattacgat gccgagaaaa tgattaacgg gcgtagtatg     120
aaagattggt taaagtttgc aatggcatgg tggcatacac tttgtgccga aggcggtgac     180
cagtttggag gcggaaccaa acagttccca tggaacggtg accctgatcc cgtgcaggca     240
gccaagaata aaatggatgc cggtttcgag tttatgcaga aaatgggcat cgggtattat     300
tgcttccatg atgtcgatct ggttacgaa gccgacagca tcgaagccta tgaggccaac     360
ttgaaagagc tggttgctta tgctaagcag aaacaggccg aaacaggcat caaactgttg     420
tggggaacgg ccaatgtatt cagccacgcg cgttacatga acggtgcagc caccaatccc     480
gattttgatg ttgtggcccg tgccgctgtc cagataaaga atgcgattga tgccaccatt     540
gaactgggag gtacgaacta tgtcttttgg ggtggacgcg aaggctatat gtcgttgctg     600
aatactgatc agaaacgcga aaaagaacat ctggcacaga tgctgaccat tgcccgtgat     660
tatggacgtg cacgtggttt caagggcact ttcctgattg aaccgaaacc catggaaccg     720
acaaagcatc agtatgatgt cgatacagag acagttatcg gcttcctgaa ggctcacgga     780
ctgaatcaag acttcaaagt gaatatcgaa gtgaatcatg ccaccccttgc aggacatacg     840 ttcgaacatg aactggcggt ggctgtagac aacggaatgt tggggtctat cgacgcaaac     900
cgcggcgatt atcagaacgg atgggatacg gatcaatttc cgattgacaa cttcgaactg     960
acacaagcca tgatgcagat tatccgtaac gacggattag gtaacggcgg tacaaacttc    1020
gatgccaaaa ctcgccggaa ctctactgac ccggaagata tctttatcgc acatattgcc    1080
ggaatggatg ctatggcacg tgccttggaa agcgcagcca atctgctcaa tgagtctcct    1140
taccagaaaa tgttgtccga ccgttatgcc tcgttcgatg cgggcaaagg caaggagttc    1200
gaagaaggga aactcagcct ggaggaactg gttgcttatg ccaaagccaa cggagagccg    1260
aagcagacca gcggccaaca ggaactgtat gaagcactcg ttaatatcta ctcattataa    1320

<210> SEQ ID NO 2
<211> LENGTH: 439
<212> TYPE: PRT
<213> ORGANISM: Bacteroides fragilis
```

<400> SEQUENCE: 2

```
Met Ala Thr Lys Glu Tyr Phe Pro Gly Ile Gly Lys Ile Lys Phe Glu
1               5                   10                  15

Gly Lys Asp Ser Lys Asn Pro Met Ala Phe Arg Tyr Tyr Asp Ala Glu
            20                  25                  30

Lys Met Ile Asn Gly Arg Ser Met Lys Asp Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Gln Phe Pro Trp Asn Gly Asp Pro Asp Pro Val Gln Ala
65                  70                  75                  80

Ala Lys Asn Lys Met Asp Ala Gly Phe Glu Phe Met Gln Lys Met Gly
            85                  90                  95

Ile Gly Tyr Tyr Cys Phe His Asp Val Asp Leu Val Thr Glu Ala Asp
        100                 105                 110

Ser Ile Glu Ala Tyr Glu Ala Asn Leu Lys Glu Leu Val Ala Tyr Ala
    115                 120                 125

Lys Gln Lys Gln Ala Glu Thr Gly Ile Lys Leu Leu Trp Gly Thr Ala
130                 135                 140

Asn Val Phe Ser His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
            165                 170                 175

Asp Ala Thr Ile Glu Leu Gly Gly Thr Asn Tyr Val Phe Trp Gly Gly
        180                 185                 190

Arg Glu Gly Tyr Met Ser Leu Leu Asn Thr Asp Gln Lys Arg Glu Lys
    195                 200                 205

Glu His Leu Ala Gln Met Leu Thr Ile Ala Arg Asp Tyr Gly Arg Ala
210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
            245                 250                 255

Lys Ala His Gly Leu Asn Gln Asp Phe Lys Val Asn Ile Glu Val Asn
        260                 265                 270

His Ala Thr Leu Ala Gly His Thr Phe Glu His Glu Leu Ala Val Ala
    275                 280                 285

Val Asp Asn Gly Met Leu Gly Ser Ile Asp Ala Asn Arg Gly Asp Tyr
290                 295                 300

Gln Asn Gly Trp Asp Thr Asp Gln Phe Pro Ile Asp Asn Phe Glu Leu
305                 310                 315                 320

Thr Gln Ala Met Met Gln Ile Ile Arg Asn Asp Gly Leu Gly Asn Gly
            325                 330                 335

Gly Thr Asn Phe Asp Ala Lys Thr Arg Arg Asn Ser Thr Asp Pro Glu
        340                 345                 350

Asp Ile Phe Ile Ala His Ile Ala Gly Met Asp Ala Met Ala Arg Ala
    355                 360                 365

Leu Glu Ser Ala Ala Asn Leu Leu Asn Glu Ser Pro Tyr Gln Lys Met
370                 375                 380

Leu Ser Asp Arg Tyr Ala Ser Phe Asp Ala Gly Lys Gly Lys Glu Phe
385                 390                 395                 400

Glu Glu Gly Lys Leu Ser Leu Glu Glu Leu Val Ala Tyr Ala Lys Ala
```

```
                 405                 410                 415
Asn Gly Glu Pro Lys Gln Thr Ser Gly Gln Gln Glu Leu Tyr Glu Ala
            420                 425                 430

Leu Val Asn Ile Tyr Ser Leu
        435

<210> SEQ ID NO 3
<211> LENGTH: 1320
<212> TYPE: DNA
<213> ORGANISM: Bacteroides fragilis

<400> SEQUENCE: 3
atgtctacaa aagagtactt cccgggtata gggaaaatta aatttgaagg aaaagacagt    60
aagaacccga tggcatttcg ctattacgat gccgagaaaa tgattaacgg cgtagtatg   120 aaagattggt taaagtttgc aatggcatgg tggcatacac tttgtgccga aggcggtgac   180
cagtttggag gcggaaccaa acagttccca tggaacggtg accctgatcc cgtgcaggca   240
gccaagaata aaatggatgc cggtttcgag tttatgcaga aatgggcat cgggtattat    300 tgcttccatg atgtcgatct ggttacggaa gccgacagca tcgaagccta tgaggccaac   360
ttgaaagagc tggttgctta tgctaagcag aaacaggccg aaacaggcat caaactgttg   420
tggggaacgg ccaatgtatt cagccacgcg cgttacatga acgtgcagc caccaatccc    480 gattttgatg ttgtggcccg tgccgctgtc cagataaaga atgcgattga tgccaccatt   540
gaactgggag gtacgaacta tgtcttttgg ggtggacgcg aaggctatat gtcgttgctg   600
aatactgatc agaaacgcga aaagaacat ctggcacaga tgctgaccat tgcccgtgat    660
tatggacgtg cacgtggttt caagggcact ttcctgattg aaccgaaacc catggaaccg   720
acaaagcatc agtatgatgt cgatacgag acagttatcg gcttcctgaa ggctcacgga    780
ctgaatcaag acttcaaagt gaatatcgaa gtgaatcatg ccaccttgc aggacatacg    840 ttcgaacatg aactggcggt ggctgtagac aacggaatgt tggggtctat cgacgcaaac   900
cgcggcgatt atcagaacgg atgggatacg atcaatttc cgattgacaa cttcgaactg    960
acacaagcca tgatgcagat tatccgtaac gacggattag gtaacggcgg tacaaacttc   1020
gatgccaaaa ctcgccggaa ctctactgac ccggaagata tctttatcgc acatattgcc   1080
ggaatggatg ctatggcacg tgccttggaa agcgcagcca atctgctcaa tgagtctcct   1140
taccagaaaa tgttgtccga ccgttatgcc tcgttcgatg cgggcaaagg caaggagttc   1200
gaagaaggga aactcagcct ggaggaactg gttgcttatg ccaaagccaa cggagagccg   1260
aagcagacca gcggccaaca ggaactgtat gaagcactcg ttaatatcta ctcattataa   1320

<210> SEQ ID NO 4
<211> LENGTH: 439
<212> TYPE: PRT
<213> ORGANISM: Bacteroides fragilis

<400> SEQUENCE: 4

Met Ser Thr Lys Glu Tyr Phe Pro Gly Ile Gly Lys Ile Lys Phe Glu
1               5                   10                  15

Gly Lys Asp Ser Lys Asn Pro Met Ala Phe Arg Tyr Tyr Asp Ala Glu
            20                  25                  30

Lys Met Ile Asn Gly Arg Ser Met Lys Asp Trp Leu Lys Phe Ala Met
        35                  40                  45

Ala Trp Trp His Thr Leu Cys Ala Glu Gly Gly Asp Gln Phe Gly Gly
    50                  55                  60
```

```
Gly Thr Lys Gln Phe Pro Trp Asn Gly Asp Pro Asp Pro Val Gln Ala
 65                  70                  75                  80

Ala Lys Asn Lys Met Asp Ala Gly Phe Glu Phe Met Gln Lys Met Gly
                 85                  90                  95

Ile Gly Tyr Tyr Cys Phe His Asp Val Asp Leu Val Thr Glu Ala Asp
            100                 105                 110

Ser Ile Glu Ala Tyr Glu Ala Asn Leu Lys Glu Leu Val Ala Tyr Ala
        115                 120                 125

Lys Gln Lys Gln Ala Glu Thr Gly Ile Lys Leu Leu Trp Gly Thr Ala
130                 135                 140

Asn Val Phe Ser His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Gln Met Leu Thr Ile Ala Arg Asp Tyr Gly Arg Ala
210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Gly Leu Asn Gln Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
290                 295                 300

Gln Asn Gly Trp Asp Thr Asp Gln Phe Pro Ile Asp Asn Phe Glu Leu
305                 310                 315                 320

Thr Gln Ala Met Met Gln Ile Ile Arg Asn Asp Gly Leu Gly Asn Gly
                325                 330                 335

Gly Thr Asn Phe Asp Ala Lys Thr Arg Arg Asn Ser Thr Asp Pro Glu
            340                 345                 350

Asp Ile Phe Ile Ala His Ile Ala Gly Met Asp Ala Met Ala Arg Ala
        355                 360                 365

Leu Glu Ser Ala Ala Asn Leu Leu Asn Glu Ser Pro Tyr Gln Lys Met
370                 375                 380

Leu Ser Asp Arg Tyr Ala Ser Phe Asp Ala Gly Lys Gly Lys Glu Phe
385                 390                 395                 400

Glu Glu Gly Lys Leu Ser Leu Glu Glu Leu Val Ala Tyr Ala Lys Ala
                405                 410                 415

Asn Gly Glu Pro Lys Gln Thr Ser Gly Gln Gln Glu Leu Tyr Glu Ala
            420                 425                 430

Leu Val Asn Ile Tyr Ser Leu
        435

<210> SEQ ID NO 5
<211> LENGTH: 1319
<212> TYPE: DNA
<213> ORGANISM: Bacteroides fragilis
```

```
<400> SEQUENCE: 5
tgtctacgaa ggaatacttc ccaggcatcg gtaagatcaa attcgaagga aaggattcaa        60
agaatccaat ggcattcaga tactacgacg ctgagaagat gatcaacggc agaagtatga       120
aggactggtt gaaattcgca atggcttggt ggcatactct ttgtgccgag ggtggagatc       180
aatttggtgg aggtacaaag caatttccat ggaacggaga cccagatcct gtccaagctg       240
ccaagaataa gatggatgct ggttttgaat tcatgcaaaa aatgggcatt gggtattact       300
gtttccatga tgttgatttg gttacagaag ctgattctat cgaagcttac gaagctaact       360
tgaaagaatt agtcgcctat gccaagcaaa agcaggctga aactggcatt aaattgttat       420
ggggaacggc aaatgttttc tcacacgctc gttatatgaa tggcgctgct actaatccgg       480
attttgacgt tgtagcaaga gcggctgtcc aaatcaagaa cgctattgat gcaacaatag       540
aattaggtgg gactaattat gttttttggg gcggcaggga aggttacatg agccttctga       600
acaccgacca gaaaagggaa aaagagcact tagcccaaat gttgactatc gccagagatt       660
acgggagagc cagaggattt aaaggtactt tcttgataga acctaagcct atggaaccaa       720
ctaaacacca atacgatgtc gatactgaaa ctgttattgg tttttttaaaa gcgcacggtc      780 taaatcagga ctttaaagtt aacatagaag ttaatcacgc gactctagct ggtcacactt       840
tcgagcatga actagcagta gctgttgata acggaatgct tggctctatc gatgcaaaca       900
gaggtgatta tcaaaacggt tgggataccg atcaatttcc aatcgataat ttcgagttga       960
cccaagctat gatgcaaatc attaggaacg atggtttagg caatggagga accaactttg      1020
atgcaaagac tcgtagaaac tcaacagatc ccgaagatat tttcattgct cacatcgctg      1080
gtatggacgc aatggctaga gccttagaat ctgctgctaa tctgttgaat gaaagcccat      1140
accaaaagat gttgagcgac cgttatgcca gttttgacgc tggaaaagga aaggaattcg      1200
aagaaggtaa attatccttg gaggagttgg ttgcgtatgc aaaagctaat ggcgaaccaa      1260
agcaaacgtc cggtcaacaa gaattgtatg aagctcttgt gaatatttac tcactgtaa       1319
```